(12) United States Patent
Nishimura et al.

(10) Patent No.: US 10,537,723 B2
(45) Date of Patent: Jan. 21, 2020

(54) MICRONEEDLE DEVICE

(71) Applicant: HISAMITSU PHARMACEUTICAL CO., INC., Tosu-shi, Saga (JP)

(72) Inventors: Shinpei Nishimura, Tsukuba (JP); Seiji Tokumoto, Tsukuba (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 15/509,398

(22) PCT Filed: Sep. 10, 2015

(86) PCT No.: PCT/JP2015/075729
§ 371 (c)(1),
(2) Date: Mar. 7, 2017

(87) PCT Pub. No.: WO2016/039418
PCT Pub. Date: Mar. 17, 2016

(65) Prior Publication Data
US 2017/0266427 A1    Sep. 21, 2017

(30) Foreign Application Priority Data

Sep. 11, 2014   (JP) ................................ 2014-185149

(51) Int. Cl.
*A61M 37/00* (2006.01)
*A61K 9/00* (2006.01)
*A61K 47/18* (2017.01)
*A61L 31/08* (2006.01)
*A61L 31/16* (2006.01)

(52) U.S. Cl.
CPC ....... *A61M 37/0015* (2013.01); *A61K 9/0021* (2013.01); *A61K 47/183* (2013.01); *A61L 31/08* (2013.01); *A61L 31/16* (2013.01); *A61L 2300/252* (2013.01); *A61M 37/00* (2013.01);
(Continued)

(58) Field of Classification Search
CPC ...... A61M 37/0015; A61M 2037/0023; A61K 9/0021
See application file for complete search history.

(56) References Cited

U.S. PATENT DOCUMENTS

2005/0025778 A1   2/2005   Cormier et al.
2006/0040864 A1   2/2006   Ameri et al.
(Continued)

FOREIGN PATENT DOCUMENTS

CN    101048151 A    10/2007
CN    102088935 A    6/2011
(Continued)

OTHER PUBLICATIONS

International Search Report dated Oct. 27, 2015 corresponding to International application No. PCT/JP2015/075729.
(Continued)

*Primary Examiner* — Shefali D Patel
(74) *Attorney, Agent, or Firm* — Nath, Goldberg & Meyer; Joshua B. Goldberg; Tanya E. Harkins (57) ABSTRACT

The present invention provides a microneedle device comprising: a substrate; a microneedle disposed on the substrate; and a coating layer formed on the microneedle; wherein the coating layer comprises a physiologically active substance, arginine, and glycerin.

2 Claims, 3 Drawing Sheets (52) U.S. Cl.
CPC ............... *A61M 2037/0023* (2013.01); *A61M 2037/0046* (2013.01); *A61M 2037/0053* (2013.01)

(56) References Cited

U.S. PATENT DOCUMENTS

| | | |
|---|---|---|
| 2006/0188555 A1 | 8/2006 | Cormier et al. |
| 2008/0108557 A1 | 5/2008 | Behrens et al. |
| 2009/0291473 A1 | 11/2009 | Sugimura et al. |
| 2011/0190688 A1 | 8/2011 | Tagliaferri et al. |
| 2011/0288485 A1 | 11/2011 | Tokumoto et al. |
| 2012/0330250 A1 | 12/2012 | Kuwahara et al. |
| 2013/0123707 A1 | 5/2013 | Determan et al. |
| 2013/0323293 A1 | 12/2013 | Umemoto et al. |
| 2014/0066842 A1 | 3/2014 | Zhang et al. |
| 2014/0066843 A1 | 3/2014 | Zhang et al. |
| 2015/0314117 A1 | 11/2015 | Arami et al. |
| 2015/0374620 A1 | 12/2015 | Sugahara et al. |

FOREIGN PATENT DOCUMENTS

| | | | |
|---|---|---|---|
| CN | 102770176 A | 11/2012 | |
| CN | 103391798 A | 11/2013 | |
| CN | 103402496 A | 11/2013 | |
| CN | 103429222 A | 12/2013 | |
| EP | 3192556 A1 | 7/2017 | |
| JP | 2523843 B2 | 5/1996 | |
| JP | 2001323000 A | 11/2001 | |
| JP | 2007521092 A | 8/2007 | |
| JP | 2008510520 A | 4/2008 | |
| JP | 2008528509 A | 7/2008 | |
| JP | 2009273427 A | 11/2009 | |
| JP | 2011516166 A | 5/2011 | |
| JP | 2013107885 A | 6/2013 | |
| JP | 2014507473 A | 3/2014 | |
| JP | 2014514022 A | 6/2014 | |
| TW | 201247260 A1 | 12/2012 | |
| WO | 8810270 A1 | 12/1988 | |
| WO | 2010074239 A1 | 7/2010 | |
| WO | 2011105496 A1 | 1/2011 | |
| WO | 2012115207 A1 | 8/2012 | |
| WO | 2012115208 A1 | 8/2012 | |
| WO | WO 2012122163 A1 * | 9/2012 | ........... A61K 9/0021 |
| WO | 2013082418 A1 | 6/2013 | |
| WO | 2013151044 A1 | 10/2013 | |
| WO | 2014097837 A1 | 6/2014 | |
| WO | 2014126104 A1 | 8/2014 | |

OTHER PUBLICATIONS

International Search Report dated Dec. 22, 2015 corresponding to International application No. PCT/JP2015/079462.

International Preliminary Report on Patentability dated Mar. 14, 2017 issued in corresponding International Application No. PCT/JP2015/075729.

English translation of the Written Opinion of the International Searching Authority dated Oct. 27, 2015 issued in corresponding International Application No. PCT/JP2015/075729.

* cited by examiner

MICRONEEDLE DEVICE

This is a National Phase Application filed under 35 U.S.C. 371 as a national stage of PCT/JP2015/075729, filed Sep. 10, 2015, an application claiming the benefit of Japanese Application No. 2014-185149, filed Sep. 11, 2014, the content of each of which is hereby incorporated by reference in its entirety.

TECHNICAL FIELD

The present invention relates to a microneedle device.

BACKGROUND ART

A microneedle device is known as one of the devices for intradermal administration of a physiologically active substance. The microneedle device has a plurality of microneedles on its main surface. As one specific aspect thereof, for example, there is a microneedle having a coating layer containing a physiologically active substance formed thereon and a self-dissolving microneedle containing a physiologically active substance (for example, Patent Literatures 1 to 4).

CITATION LIST

Patent Literature

Patent Literature 1: WO 2011/105496
Patent Literature 2: WO 2012/115207
Patent Literature 3: WO 2012/115208
Patent Literature 4: JP 2014-507473 A

SUMMARY OF INVENTION

Technical Problem

In the case of a microneedle device in which a coating layer containing a physiologically active substance is formed on each microneedle, it is difficult to reproducibly apply the physiologically active substance to the coating layer of each microneedle so that the content of the substance is uniform.

When a coating agent is applied to form a coating layer, the coating layer may be cracked due to the components in the coating agent. Thus, it may be difficult to obtain sufficient strength for applying to the skin.

Therefore, an object of the present invention is to provide a microneedle device having a coating layer in which coating can be performed so that a physiologically active substance in the coating layer is uniformly dispersed and the occurrence of cracks in the coating layer can be reduced when the coating layer is formed.

Solution to Problem

The present invention provides a microneedle device comprising: a substrate; a microneedle disposed on the substrate; and a coating layer formed on the microneedle; wherein the coating layer contains a physiologically active substance, arginine, and glycerin.

The coating layer contains glycerin so that the same amount of the physiologically active substance can be reproducibly applied to the microneedles.

It is preferable that, in the coating layer, the mass of arginine is 0.06 to 0.85-fold of the mass of the physiologically active substance and the mass of glycerin is 40% or less relative to the mass of the whole coating layer. It is preferable that the coating layer further contains an acid selected from the group consisting of citric acid, phosphoric acid, boric acid, tartaric acid, and lactic acid.

Further, the present invention provides a method for producing a microneedle device including the steps of: providing a microneedle array having a substrate and a microneedle; mixing a physiologically active substance, arginine, and glycerin to obtain a coating composition; coating the microneedle with the coating composition; and drying the coating composition to form a coating layer on the microneedle.

It is preferable that the coating composition further contains an acid selected from the group consisting of citric acid, phosphoric acid, boric acid, tartaric acid, and lactic acid.

It is preferable that the drying is performed until, in the coating layer, the mass of arginine reaches 0.06 to 0.85-fold of the mass of the physiologically active substance and the mass of glycerin reaches 40% or less relative to the mass of the whole coating layer.

Further, the present invention provides a coating agent for microneedles containing a physiologically active substance, arginine, and glycerin. It is preferable that the coating agent further contains an 1.5 acid selected from the group consisting of citric acid, phosphoric acid, boric acid, tartaric acid, and lactic acid.

The present invention also provides a method comprising a step of coating each microneedle with a coating composition containing a physiologically active substance, arginine, and glycerin to form a coating layer, wherein the occurrence of cracks in the coating layer on each microneedle is reduced. It is preferable that the coating composition further contains an acid selected from the group consisting of citric acid, phosphoric acid, boric acid, tartaric acid, and lactic acid.

The present invention also provides a method comprising a step of coating each microneedle with a coating composition containing a physiologically active substance, arginine, and glycerin to form a coating layer, wherein the content of the components contained in the coating layer on each microneedle is uniformly dispersed. It is preferable that the coating composition further contains an acid selected from the group consisting of citric acid, phosphoric acid, boric acid, tartaric acid, and lactic acid.

Advantageous Effects of Invention

According to the present invention, the same amount of the physiologically active substance can be reproducibly applied to the microneedles. Further, according to the present invention, when the coating layer is formed, the occurrence of cracks of the coating layer can be reduced, thereby improving the productivity of the microneedle device.

BRIEF DESCRIPTION OF DRAWINGS

FIGS. 3(*a*) to 3(*c*) are pattern diagrams showing one embodiment of a method for producing a microneedle device.

DESCRIPTION OF EMBODIMENTS

Hereinbelow, preferable embodiments will be explained with reference to drawings. It is to be noted that in the explanation of the drawings, the same symbols are assigned to the same elements and redundant explanation will be omitted. Also, in the drawings, some parts are exaggeratedly drawn to make understanding easy, and thus the size and ratio are not necessarily consistent with the description.

One embodiment of the present invention is a microneedle device comprising: a substrate; a microneedle disposed on the substrate; and a coating layer formed on the microneedle; wherein the coating layer contains a physiologically active substance, arginine, and glycerin.

Figure 1:
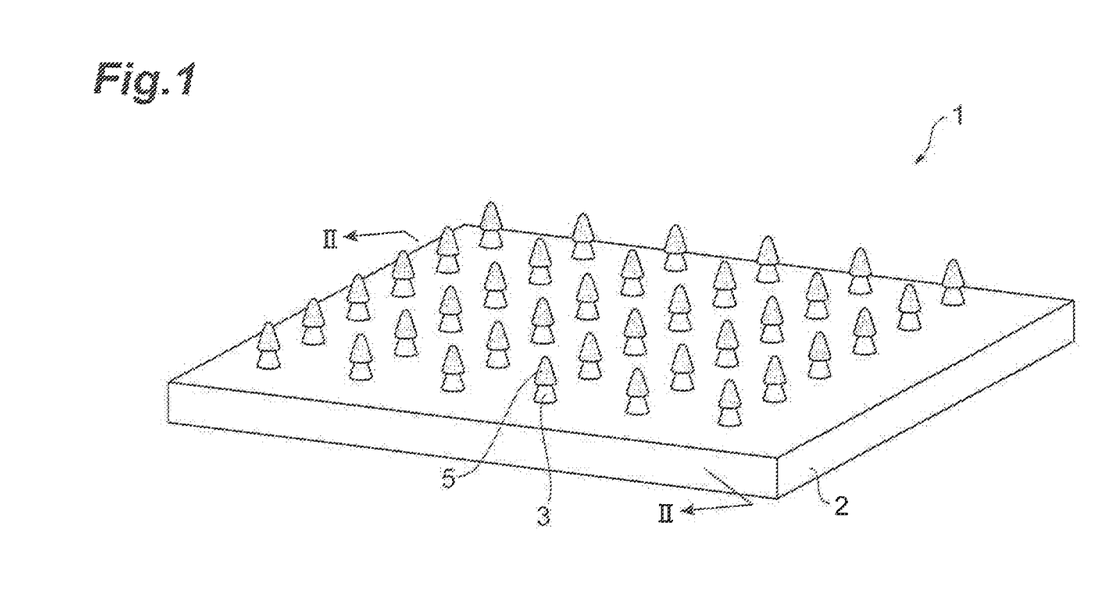
FIG. 1 is a perspective view showing one embodiment of a microneedle device.

FIG. 1 is a perspective view showing one embodiment of a microneedle device. A microneedle device 1 shown in FIG. 1 has a substrate 2, a plurality of microneedles 3 that are two-dimensionally arranged on the substrate 2, and a coating layer 5 formed on each of the microneedles 3. The coating layer 5 contains a physiologically active substance, arginine, and glycerin.

The substrate 2 is a foundation to support the microneedles 3. The area of the substrate 2 is preferably 0.5 to 10 $cm^2$, more preferably 1 to 5 $cm^2$, and still more preferably 1 to 3 $cm^2$. A substrate of a desired size may be configured by connecting a plurality of the substrates 2.

The microneedles 3 each have a minute structure, and the height (length) thereof is preferably 50 to 600 μm. At this point, the length of the microneedles 3 is set at 50 μm or more, thereby ensuring administration of the physiologically active substance contained in the coating layer. Further, the length of the microneedles 3 is set at 600 μm or less, thereby avoiding that the microneedles contact nerves so as to reduce the possibility of pain and avoid the possibility of bleeding. Also, when the length of the microneedles 3 is 500 μm or less, the amount of the physiologically active substance to enter the skin can be efficiently administered, and in certain cases, administrating without piercing the basement membrane is also possible. The length of the microneedles 3 is particularly preferably 300 to 500 μm.

At this point, a microneedle 3 refers to a projecting structure including, in a broad sense, a needle shape or a structure including a needle shape. However, the microneedle is not limited to a structure of a needle shape having a tapered tip, and may also be a structure lacking a tapered tip. When the microneedles 3 each have a conical structure, the diameter of the basal surface thereof is preferably about 50 to 200 μm. Although the microneedles 3 are each in a conical shape according to the present embodiment, microneedles may be in a polygonal pyramid shape such as a square pyramid or in other shapes.

The microneedles 3 are each typically disposed spaced apart so as to have a density of approximately 1 to 10 needles per millimeter (mm) in a row of the needles. Generally, adjacent rows are spaced apart from each other by a distance substantially equal to the space between the needles in a row, and the microneedles 3 have a needle density of 100 to 10000 needles per $cm^2$. When a needle density of 100 needles or more is achieved, the microneedles can efficiently pierce the skin. Meanwhile, a needle density of more than 10000 needles makes it difficult to maintain the strength of the microneedles 3. The density of the microneedles 3 is preferably 200 to 5000 needles, more preferably 300 to 2000 needles, and still more preferably 400 to 850 needles.

Examples of a material of the substrate 2 or the microneedles 3 include silicon, silicon dioxide, ceramics, metals (such as stainless steel, titanium, nickel, molybdenum, chromium, and cobalt) and synthetic or natural resin materials. In consideration of the antigenicity of the microneedles and the unit price of the material, a biodegradable polymer such as polylactic acid, polyglycolide, polylactic acid-co-polyglycolide, pullulan, caprolactone, polyurethane, and polyanhydride, and a synthetic or natural resin material such as polycarbonate, polymethacrylic acid, ethylenevinyl acetate, polytetrafluoroethylene, and polyoxymethylene, which are non-degradable polymers, are particularly preferable. Further, polysaccharides such as hyaluronic acid, sodium hyaluronate, pullulan, dextran, dextrin, and chondroitin sulfate are also suitable.

Examples of a production method of the substrate 2 or the microneedles 3 include wet etching process or dry etching process using a silicon substrate, precision machining using metals or resins (such as electric discharge method, laser processing, dicing processing, hot embossing process, and injection mold processing), and machinery cutting. By these processing methods, the substrate 2 and the microneedles 3 are integrally molded. Examples of a method fix hollowing the microneedles 3 include a method in which a secondary processing such as laser processing is applied after producing the microneedles 3.

Although the microneedle device 1 has the coating layer 5 on each of the microneedles 3, the coating layer 5 is preferably formed by coating with the coating composition. Examples of the coating method include spray coating and dip coating, and the dip coating is preferable. In this regard, although the coating layer 5 is formed on all the microneedles 3 in FIG. 1, the coating layer 5 may be formed on only some of the microneedles 3. Although the coating layer 5 is formed on only the tip portion of the microneedle 3 in FIG. 1, the layer may be formed so as to cover the whole microneedle 3. Further, the coating layer 5 may be formed on the substrate 2.

Figure 2:
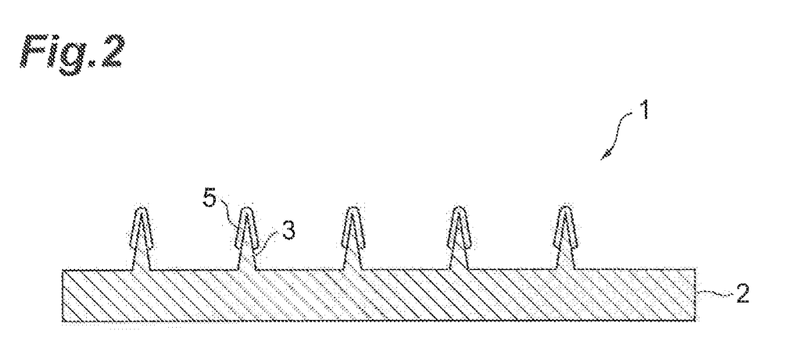
FIG. 2 is a cross-sectional side surface view of FIG. 1 taken along the line II-II.

FIG. 2 is a cross-sectional side surface view of FIG. 1 taken along the line II-II. As shown in FIG. 2, the microneedle device 1 has the substrate 2, the microneedles 3 disposed on the substrate 2, and the coating layer 5 formed on each of the microneedles 3. The coating layer 5 formed on each of the microneedles contains a physiologically active substance, arginine, and glycerin.

The mass of arginine contained in the coating layer is preferably 0.06 to 0.85-fold, more preferably 0.1 to 0.65-fold, still more preferably 0.1 to 0.5-fold of the mass of the physiologically active substance. The mass of arginine is 0.06-fold or more of the mass of the physiologically active substance, whereby the occurrence of cracks in the coating layer can be reduced when the coating layer is formed. Consequently, the productivity of the microneedle device is further improved.

Further, the mass of arginine contained in the coating layer is preferably 0.1% to 40%, more preferably 3 to 33%, and still more preferably 7 to 25% relative to the mass of the whole coating layer.

The mass of glycerin contained in the coating layer is 40% or less based on the mass of the whole coating layer, From the viewpoint of practical utility, it is 10% or more. Further, the mass of glycerin is preferably 10 to 40%, more preferably 15 to 40%, and still more preferably 15 to 35%.

The mass of glycerin contained in the coating layer is preferably 2-fold or less, more preferably 1.5-fold or less, and still more preferably 1-fold or less of the mass of the physiologically active substance.

With respect to the mass of each of the components contained in the coating layer, the content of glycerin is measured by, for example, gas chromatography, and based on its value, the content of other components can be calculated.

The coating layer can be formed using, for example, a coating composition containing a physiologically active substance, arginine and glycerin.

The physiologically active substance is not particularly limited as long as it is a substance which exerts a therapeutic or prophylactic effect in a subject to be administered. Examples of the physiologically active substance include peptides, proteins, DNAs, RNAs, sugars, nucleic acids, and glycoproteins. Particularly, when the physiologically active substance is a glycoprotein, the coating layer can be formed more efficiently.

Specific examples of the physiologically active substance include interferon-α, interferon-β for multiple sclerosis, erithropoietin, follitropin-β, follitropin-α, G-CSF, GM-CSF, human chorionic gonadotropin, leutinizing hormone, follicle stimulating hormone (FSH), calcitonin salmon, glucagon, GNRH antagonist, insulin, LHRH (luteal hormone releasing hormone), human growth hormone, parathyroid hormone, filgrastim, heparin, low molecular weight heparin, somatropin, incretin, GLP-1 analog (for example, exenatide, liraglutide, lixisenatide, albiglutide, and taspoglutide), venom peptide analog, γ-globulin, Japanese encephalitis vaccine, rotavirus vaccine, Alzheimer's disease vaccine, arteriosclerosis vaccine, cancer vaccine, nicotine vaccine, diphtheria, vaccine, tetanus vaccine, pertussis vaccine, Lyme disease vaccine, rabies vaccine, diplococcus-pneumoniae vaccine, yellow fever vaccine, cholera vaccine, vaccinia vaccine, tuberculosis vaccine, rubella vaccine, measles virus vaccine, influenza vaccine, mumps vaccine, botulinus vaccine, herpesvirus vaccine, other DNA vaccines, and hepatitis B vaccine.

The content of the physiologically active substance in the coating composition is preferably 20 to 70% by mass, more preferably 25 to 50% by mass, and still more preferably 20 to 45% by mass based on the mass of the whole coating composition. When the content of the physiologically active substance is 20% by mass or more, a pharmacological action of the physiologically active substance is sufficiently exerted, thereby easily producing a desired therapeutic effect.

The content of arginine in the coating composition is preferably 0.05 to 2-fold, more preferably 0.05 to 1-fold, and still more preferably 0.1 to 0.5-fold of the mass of the physiologically active substance contained in the coating composition. The content of arginine is 0.05-fold or more of the mass of the physiologically active substance, thereby making cracks in the coating layer less likely to occur. Further, the content of arginine is 2-fold or less, thereby further improving the solubility of the physiologically active substance in the coating composition.

The coating composition contains glycerin so that the content uniformity of the physiologically active substance in the coating composition under the coating conditions (for example, room temperature) is improved. Here, the phrase "lack of content uniformity" means that when the coating composition is applied to the microneedles, the content of the physiologically active substance in the coating composition becomes non-uniform with remarkable changes in physical properties of the coating composition due to volatilization of a solvent (for example, a phenomenon such as generation of concentration gradient or impossibility of applying to microneedles after drying). The content uniformity of the physiologically active substance is improved, whereby the physiologically active substance is stably released from the coating layer during the use of the microneedle device and a desired therapeutic effect can be continuously obtained. Further, glycerin having a high viscosity is contained so that the coating layer is easily supported on the tip of the microneedle. In this regard, glycerin is a component that volatilizes when reduced-pressure drying is performed. The glycerin itself does not solidify.

The content of glycerin in the coating composition is preferably 0.8 to 2-fold, more preferably 1 to 2-fold, and still more preferably 1 to 1.5-fold of the mass of the physiologically active substance contained in the coating composition. More preferred is a case in which the content of glycerin is 0.8-fold or more of the mass of the physiologically active substance, because the content uniformity and solubility of the physiologically active substance in the coating layer are excellent and the dripping is less likely to occur when being applied to the microneedles.

Further, the coating composition preferably contains an acid selected from the group consisting of citric acid, phosphoric acid, boric acid, tartaric acid, and lactic acid. Particularly, the coating composition more preferably contains citric acid. The coating composition contains a specific acid so that the basicity of arginine can be neutralized, and the pH of the composition can be adjusted to a desired range.

The content of the acid is preferably 0.1 to 20% by mass, more preferably 0.5 to 10% by mass, and still more preferably 1 to 7% by mass based on the mass of the whole coating composition.

Further, the content of the acid is preferably 0.01 to 1-fold, more preferably 0.05 to 0.8-fold, and still more preferably 0.1 to 0.5-fold of the mass of arginine contained in the coating composition.

The coating composition may further contain a solvent, a polymeric carrier (thickening agent), a solubilizing agent, an absorption promoter, a stabilizer, an antioxidant, azo emulsifier, a surfactant, and a compound such as a salt, as needed. Examples of the solvent include water such as purified water and distilled water and alcohols such as methanol and ethanol. The coating composition contains a solvent so that the handling properties when applied to the microneedles can be improved and the solvent can be easily removed by the drying step.

When the coating composition contains a solvent, the solvent is removed in the drying step. Accordingly, the composition ratio of the components in the coating composition is not necessarily reflected in the coating layer.

Hence, when a microneedle device is produced, the coating layer is formed by drying the coating composition applied to the microneedles. In the drying step, the solvent contained in the coating composition is removed and the content of glycerin may also decrease. Further, the coating layer is formed by reduced-pressure drying, whereby the content of glycerin decreases and the concentration of the physiologically active substance contained in the coating layer tends to increase.

With respect to the time required to dry the applied coating composition, the drying is preferably performed until the mass of glycerin reaches 40% or less relative to the mass of the whole coating layer. Specifically, the mass of glycerin decreases, preferably by 25% or more, more preferably by 33% or more, and still more preferably by 50% or more relative to the mass of glycerin contained in the composition applied to the microneedles. Further, the drying time is preferably 1 hour or longer, the drying is performed more preferably for 3 hours or longer, still more preferably 5 hours or longer, particularly preferably 10 hours or longer, and extremely preferably 15 hours or longer.

Examples of the polymeric carrier include polyethylene oxide, polyhydroxymethylcellulose, hydroxypropylcellulose, polyhydroxypropylmethylcellulose, polymethylcellulose, dextran, polyethylene glycol, polyvinyl alcohol, polyvinylpyrrolidone, carmellose sodium, chondroitin sulfate, hyaluronic acid, dextran, and gum arabic. The weight average molecular weight of polyethylene glycol to be used as a polymeric carrier preferably exceeds 600 but is 500000 or less. As the polymeric carrier, a carrier highly compatible (having properties of being uniformly mixed) with a physiologically active substance is preferable. Particularly preferred are hydroxypropylcellulose, dextran, polyvinyl alcohol, pullulan, and the like.

The content of the polymeric carrier in the coating composition 10 is 0.005 to 30% by mass, preferably 0.01 to 20% by mass, and more preferably 0.05 to 10% by mass based on the total mass of the coating composition 10. The polymeric carrier may need to have a certain degree of viscosity that does not cause dripping and the viscosity is preferably 100 to 100000 mPa·s at room temperature (25° C.). A more preferable viscosity is 500 to 60000 mPa·s.

In addition to the above, to the coating composition 10, propylene carbonate, crotamiton, L-menthol, peppermint oil, limonene, diisopropyl adipate, and the like may be added as a solubilizing aid or absorption promoter, and methyl salicylate, glycol salicylate, L-menthol, thymol, peppermint oil, nonylic acid vanillylamide, chili pepper extract, and the like may be added as an efficacy supplement as needed.

The surfactant may be either a nonionic surfactant or an ionic surfactant (cationic, anionic, and amphoteric); however, from the safety aspect, a nonionic surfactant, which is normally used for a pharmaceutical base, is desirable. Examples of these compounds include sugar alcohol fatty acid ester such as sucrose fatty acid ester, propylene glycol fatty acid ester, polyoxyethylene sorbitan fatty acid ester, polyoxyethylene glycerin fatty acid ester, polyethylene glycol fatty acid ester, polyoxyethylene castor oil, and polyoxyethylene hydrogenated castor oil.

A method for producing a microneedle device comprises the steps of: providing a microneedle array that has a substrate and a microneedle; mixing a physiologically active substance, arginine, and glycerin to obtain a coating composition; coating the microneedle with the coating composition; and drying the coating composition to form a coating layer on the microneedle.

Subsequently, the method for producing a microneedle device will be explained with reference to FIGS. 3(a) to 3(c). In this regard, the production method shown in FIGS. 3(a) to 3(c) is also referred to as "dip method using a mask plate".

Figure 3:
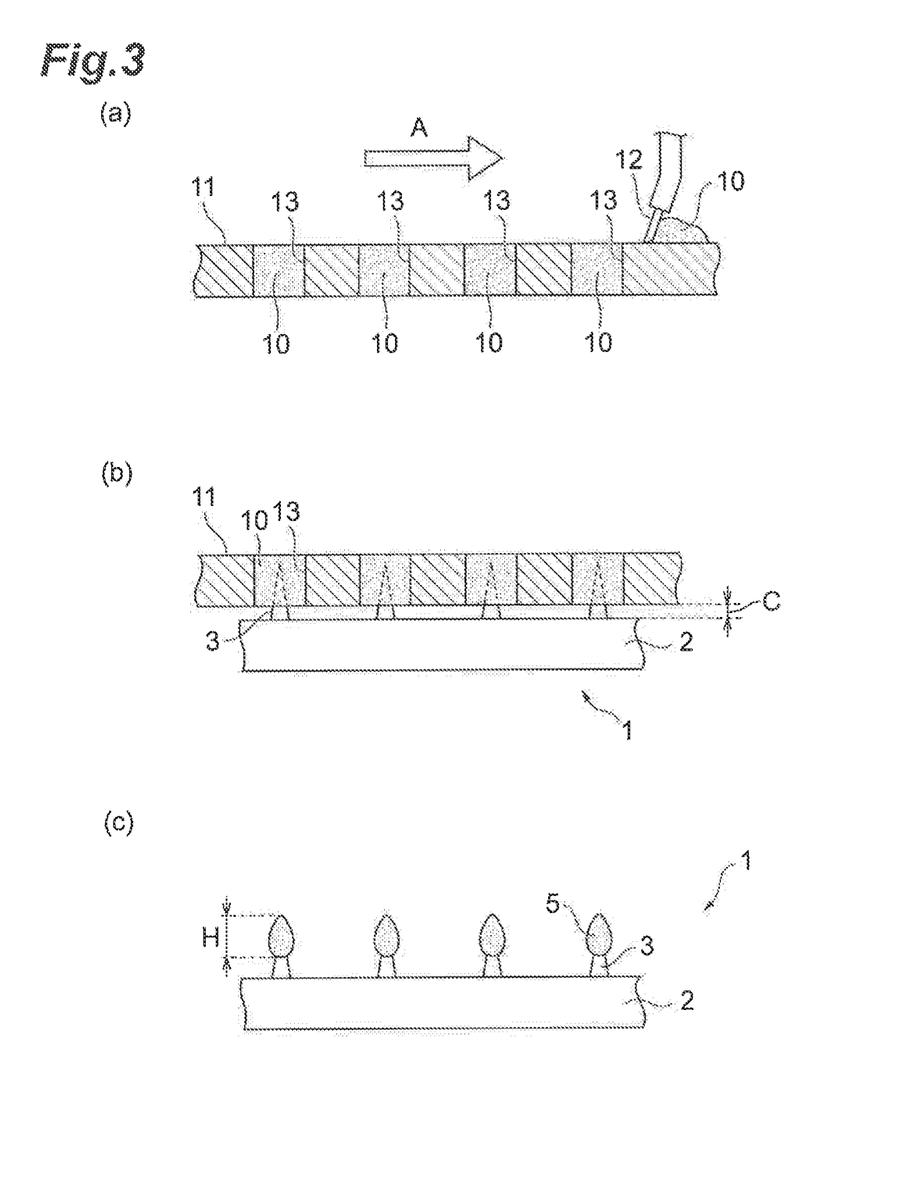

FIGS. 3(a) to 3(c) are pattern diagrams showing one embodiment of a method for producing a microneedle device. According to this method, first of all, as shown in FIG. 3(a), the coating composition 10 is swept with a spatula 12 in the direction of the arrow A on a mask plate 11. By doing so, openings 13 are filled with the coating composition 10. Subsequently, as shown in FIG. 3(b), the microneedles 3 are inserted into the openings 13 of the mask plate 11. Thereafter, as shown in FIG. 3(c), the microneedles 3 are pulled out from the openings 13 of the mask plate 11. By doing so, the coating composition 10 adheres to the microneedles 3. In this regard, the coating composition 10 may adhere to the substrate 2. The volatile substance in the coating composition 10 on the microneedles 3 is removed by a method such as air drying, reduced-pressure drying (vacuum drying), or a combination of these methods. By the above process, the coating layer 5 strongly adheres to each of the microneedles 3, and typically becomes glassy or solid, whereby the microneedle device 1 is produced. The water content in the coating layer 5 is normally 55% by mass or less, preferably 30% by mass or less, and more preferably 10% by mass or less based on the total amount of the coating layer 5. By the above method, dripping of the coating composition 10 after being coated is prevented. The dripping indicates dripping of the coating composition from needle tips and means that an H part in FIG. 3(c) lengthens.

The height H of the coating layer 5 formed on each of the microneedles 3 is adjusted by a clearance (gap) C shown in FIG. 3(b). This clearance C is defined as a distance between the basal surface of the microneedles 3 and the surface of the mask plate 11 (a thickness of the substrate 2 is not involved), and is set according to a tension of the mask plate 11 and the length of the microneedles 3. The range of the distance of clearance C is preferably 0 to 500 µm. When a distance of clearance C is 0, it means that the coating composition 10 is applied to the entire microneedles 3. Although the height H of the coating composition 10 formed on the microneedles 3 varies depending on the height H of the microneedles 3, the height H is normally 10 to 500 µm, preferably 30 to 300 µm, and more preferably 40 to 250 µm. In order to effectively administer the physiologically active substance in the coating composition 10 to the skin, the substance is preferably concentrated in a part of the microneedle 3 (i.e., the tip portion of the microneedle 3). From viewpoints of the stimulation to the skin and the transferring efficiency of the physiologically active substance to the skin, it is preferable to allow the substance to be located at up to 200 µm from the tip of the microneedle 3. When the coating composition 10 has a high viscosity, the coating layer 5 is easily formed on a part of the microneedle. By the method, the coating composition 10 adhering to the microneedles 3 after removal of its volatile components can form preferably an approximately spherical or teardrop shaped coating layer 5 at the tip portion of the microneedle 3. Then, the coating composition is inserted into the skin at the same time when the microneedles 3 pierce the skin.

The thickness of the dried coating layer 5 is preferably less than 50 µm, more preferably less than 40 µm, and still more preferably 1 to 30 µm. Generally, the thickness of the coating layer 5 refers to an average thickness as measured over the surface of the microneedle 3 after drying. The thickness of the coating layer 5 can be optionally increased by applying a plurality of films of the coating composition 10, namely, by repeatedly performing the step of coating with the coating composition 10.

When the microneedle 3 is coated with the coating composition 10, temperature and humidity in an installation environment of an apparatus are preferably controlled at a constant level. When the coating composition 10 contains water, the environment may be filled with water, as needed. By doing so, evaporation of the water in the coating composition 10 can be prevented as much as possible.

EXAMPLE

Hereinbelow, the present invention will be more specifically described by providing Examples.

(1) Content Uniformity Test

The coating compositions of Reference Examples 1 to 4 prepared according to the description of Table 1 were applied to twenty microneedle sheets by the dip method using a mask plate. In this regard, used physiologically active substances were dextran 40 (in Reference Examples 1 and 3), γ-globulin (in Reference Example 2), and bovine serum albumin (BSA) (in Reference Example 4). As a tracer, benzoic acid was added to each of Reference Examples for HPLC measurement. Each number in Table 1 means mass percent relative to the whole coating composition.

Subsequently, the coating compositions applied to the microneedles were individually recovered. The content of benzoic acid in each of the coating compositions was measured to calculate the content of the physiologically active substance. The average, standard deviation (SD), and coefficient of variation (CV) of the content of the resulting physiologically active substance were calculated. In this regard, the coefficient of variation (CV) is a value obtained by dividing the standard deviation by the average.

TABLE 1

|  | Reference Example 1 | Reference Example 2 | Reference Example 3 | Reference Example 4 |
|---|---|---|---|---|
| Dextran 40 | 49 | — | 29 | — |
| γ-globulin | — | 29 | — | — |
| BSA | — | — | — | 34 |
| Glycerin | — | 52.5 | 52.5 | 48.75 |
| Water | 50 | 17.5 | 17.5 | 16.25 |
| Benzoic acid | 1 | 1 | 1 | 1 |
| Total | 100 | 100 | 100 | 100 |

The results are shown in Table 2. In the case of using the coating compositions of Reference Examples 2 to 4 containing glycerin, both the standard deviation and coefficient of variation decreased, compared to the case of using the coating composition of Reference Example 1. Therefore, it is considered that the coating composition contains glycerin so that the content uniformity of the physiologically active substance in the coating layer is improved.

TABLE 2

|  | Reference Example 1 | Reference Example 2 | Reference Example 3 | Reference Example 4 |
|---|---|---|---|---|
| Average [μg] | 47.2 | 15.8 | 52.1 | 33.5 |
| Standard deviation (SD) [μg] | 4.9 | 1.2 | 2.4 | 1.2 |
| Coefficient of variation (CV) [%] | 10.3 | 7.3 | 4.7 | 3.7 |

(2) Influence of Content of Arginine

BSA, L-arginine, citric acid, glycerin, and water were mixed according to the description of Table 3 to prepare coating compositions of Examples 1 to 9 and Comparative Example 1. In this regard, BSA was used as the physiologically active substance. Each number in Table 3 means "% by mass". Each of the obtained coating compositions was applied to the tip of the microneedle by the dip method using a mask plate. Subsequently, each of the applied coating compositions was dried under reduced pressure to form a coating layer. The content of glycerin in the coating layer was quantified by gas chromatography (GC) analysis. Further, the property of the coating layer (crack state) was observed using the digital microscope (KEYENCE CORPORATION.) and evaluated in accordance with the following evaluation criteria:

<Evaluation Criteria>

Good: No cracks;

Poor: Any cracks are present on the surface; and

Bad: Any cracks are present on the surface and the coating layer is partially chipped.

TABLE 3

|  | BSA | L-arginine | Citric acid | Glycerin | Water | Total |
|---|---|---|---|---|---|---|
| Comparative Example 1 | 50.0 | — | — | 40.0 | 10.0 | 100.0 |
| Example 1 | 46.7 | 2.5 | 0.8 | 40.0 | 10.0 | 100.0 |
| Example 2 | 43.3 | 5.0 | 1.7 | 40.0 | 10.0 | 100.0 |
| Example 3 | 40.0 | 7.5 | 2.5 | 40.0 | 10.0 | 100.0 |
| Example 4 | 36.7 | 10.0 | 3.3 | 40.0 | 10.0 | 100.0 |
| Example 5 | 33.3 | 12.5 | 4.2 | 40.0 | 10.0 | 100.0 |
| Example 6 | 30.0 | 15.0 | 5.0 | 40.0 | 10.0 | 100.0 |
| Example 7 | 26.7 | 17.5 | 5.8 | 40.0 | 10.0 | 100.0 |
| Example 8 | 23.3 | 20.0 | 6.7 | 40.0 | 10.0 | 100.0 |
| Example 9 | 40.0 | 10.0 | — | 40.0 | 10.0 | 100.0 |

The results are shown in Table 4. In the cases of the coating compositions of Examples 1 to 9 containing L-arginine, the occurrence of cracks was reduced during formation of the coating layer. The occurrence of cracks was significantly reduced, particularly in the cases of the coating compositions of Examples 2 to 9 having an L-arginine content of 7.3% by mass or more. During preparation of the coating compositions of Examples 1 to 7, the solubility of BSA, L-arginine, and citric acid in a mixed solvent of glycerin and water (volume ratio 4:1) was more excellent.

TABLE 4

|  | Content [% by mass] | | | |
|---|---|---|---|---|
|  | BSA | L-arginine | Glycerin | Cracks |
| Comparative Example 1 | 74.8 | 0.0 | 25.2 | X |
| Example 1 | 71.0 | 3.8 | 24.0 | Δ |
| Example 2 | 63.0 | 7.3 | 27.3 | ◯ |
| Example 3 | 62.4 | 11.7 | 22.0 | ◯ |
| Example 4 | 58.6 | 16.0 | 20.1 | ◯ |
| Example 5 | 54.5 | 20.4 | 18.3 | ◯ |
| Example 6 | 50.1 | 25.0 | 16.5 | ◯ |
| Example 7 | 44.1 | 29.0 | 17.2 | ◯ |
| Example 8 | 39.1 | 33.5 | 16.3 | ◯ |
| Example 9 | 62.4 | 15.6 | 22.0 | ◯ |

(3) Effect of Reducing Occurrence of Cracks

A physiologically active substance, L-arginine, citric acid, and aqueous glycerin were mixed according to the description of Table 5 to prepare coating compositions of Examples 10 to 13 and Comparative Examples 2 to 5. In this regard, human serum albumin (HSA), lixisenatide, luteinizing hormone-releasing hormone (LHR), or γ-globulin was used as the physiologically active substance. Further, the used aqueous glycerin has a weight ratio of water to glycerin of 20:80. Each number in Table 5 means "% by mass". Each of the obtained coating compositions was applied to the tip of the microneedle by the dip method using a mask plate. Subsequently, each of the applied coating compositions was dried under reduced pressure to form a coating layer. The content of glycerin in the coating layer was quantified by gas chromatography (GC) analysis. Further, the property of the coating layer (crack state) was observed using the digital microscope (KEYENCE CORPORATION.) and evaluated in accordance with the above evaluation criteria.

TABLE 5

| | Physiologically active substance | | L-arginine | Citric acid | Aqueous glycerin |
|---|---|---|---|---|---|
| | Kind | Content | | | |
| Comparative Example 2 | HSA | 30.0 | 0.0 | 0.0 | 70.0 |
| Example 10 | HSA | 30.0 | 3.5 | 1.2 | 65.3 |
| Comparative Example 3 | Lixisenatide | 40.0 | 0.0 | 0.0 | 60.0 |
| Example 11 | Lixisenatide | 40.0 | 4.6 | 1.5 | 53.9 |
| Comparative Example 4 | LHRH | 50.0 | 0.0 | 0.0 | 50.0 |
| Example 12 | LHRH | 50.0 | 5.8 | 1.9 | 42.3 |
| Comparative Example 5 | γ-globulin | 30.0 | 0.0 | 0.0 | 70.0 |
| Example 13 | γ-globulin | 30. | 3.5 | 1.2 | 65.3 |

The results are shown in Table 6. As shown in Table 6, when HSA, lixisenatide, LHRH or γ-globulin was used as the physiologically active substance, cracks were not generated in the coating compositions of Examples 10 to 13 containing L-arginine and citric acid during formation of the coating layer. Meanwhile, cracks were generated in the coating compositions of Comparative Examples 2 to 5 which did not contain L-arginine and citric acid during formation of the coating layer.

TABLE 6

| | Content ratio of L-arginine to physiologically active substance | Content [%] of glycerin | Cracks |
|---|---|---|---|
| Comparative Example 2 | — | 13.2 | X |
| Example 10 | 0.12 | 17.9 | ○ |
| Comparative Example 3 | — | 15.4 | X |
| Example 11 | 0.12 | 19.7 | ○ |
| Comparative Example 4 | — | 23.0 | X |
| Example 12 | 0.12 | 28.1 | ○ |
| Comparative Example 5 | — | 11.2 | X |
| Example 13 | 0.12 | 13.6 | ○ |

The coating compositions of Examples 14 to 20 were prepared according to the description of Table 7.

TABLE 7

| | Physiologically active substance | | L-arginine | Citric acid | Aqueous glycerin |
|---|---|---|---|---|---|
| | Kind | Content | | | |
| Comparative Example 14 | Parathyroid hormone | 40.0 | 5.0 | 1.5 | 53.5 |
| Comparative Example 15 | GLP-1 analog | 40.0 | 5.0 | 1.5 | 53.5 |
| Comparative Example 16 | Interferon-β | 40.0 | 5.0 | 1.5 | 53.5 |
| Comparative Example 17 | Low molecular weight heparin | 40.0 | 5.0 | 1.5 | 53.5 |
| Comparative Example 18 | Venom peptide analog | 40.0 | 5.0 | 1.5 | 53.5 |
| Comparative Example 19 | Influenza vaccine | 40.0 | 5.0 | 1.5 | 53.5 |
| Comparative Example 20 | Cancer vaccine | 40.0 | 5.0 | 1.5 | 53.5 |

(4) Content Uniformity Test

The coating composition of Example 21 prepared according to the description of Table 8 was applied to twenty microneedle sheets by the dip method using a mask plate. In this regard, bovine serum albumin (BSA) was used as the physiologically active substance and a tracer (fluorescein sodium) was added thereto for measurement with a fluorescence plate reader. Further, each number in Table 8 means mass percent relative to the whole coating composition.

Subsequently, the coating compositions applied to microneedles were respectively recovered. The content of fluorescein sodium in each of the coating compositions was measured to calculate the content of the physiologically active substance. The average, standard deviation (SD), and coefficient of variation (CV) of the content of the resulting physiologically active substance were calculated. In this regard, the coefficient of variation (CV) is a value obtained by dividing the standard deviation by the average.

TABLE 8

| | Example 21 |
|---|---|
| BSA | 30 |
| Glycerin | 60 |
| Arginine | 5 |
| Water | 15 |
| Flourescein sodium | 0.05 |

The results are shown in Table 9. The formation of the coating layer using the coating composition of Example 21 resulted in an improvement of the content uniformity of the physiologically active substance in the coating layer.

TABLE 9

| | Example 21 |
|---|---|
| Average [μg] | 36.7 |
| Standard deviation (SD) [μg] | 2.6 |
| Coefficient of variation (CV) [%] | 7.2 |

(5) Effect of Reducing Occurrence of Cracks

A physiologically active substance, L-arginine, acid, and aqueous glycerin were mixed according to the description of Tables 10 and 11 to prepare coating compositions of Examples 25 to 32. In this regard, human serum albumin (HSA), lixisenatide, luteinizing hormone-releasing hormone (LHRH) or γ-globulin was used as the physiologically active substance, and phosphoric acid or tartaric acid was used as the acid. Further, the used aqueous glycerin has a weight ratio of water to glycerin of 20:80. Each number in Tables 10 and 11 means "% by mass". Each of the obtained coating compositions was applied to the tip of the microneedle by the dip method using a mask plate. Subsequently, each of the applied coating compositions was dried under reduced pressure to form a coating layer. The content of glycerin in the coating layer was quantified by gas chromatography (GC) analysis. Further, the property of the coating layer (crack state) was observed using the digital microscope (KEYENCE CORPORATION.) and evaluated in accordance with the above evaluation criteria.

TABLE 10

|  | Physiologically active substance | Arginine | Phosphoric acid | Aqueous glycerin |
|---|---|---|---|---|
| Example 25 | HSA | 30 | 3.5 | 1.2 | 65.3 |
| Example 26 | Lixisenatide | 40 | 4.6 | 1.5 | 53.9 |
| Example 27 | LHRH | 50 | 5.8 | 1.9 | 42.3 |
| Example 28 | γ-globulin | 30 | 3.5 | 1.2 | 65.3 |

TABLE 11

|  | Physiologically active substance | Arginine | Tartaric acid | Glycerin |
|---|---|---|---|---|
| Example 29 | HSA | 30 | 3.5 | 1.2 | 65.3 |
| Example 30 | Lixisenatide | 40 | 4.6 | 1.5 | 53.9 |
| Example 31 | LHRH | 50 | 5.8 | 1.9 | 42.3 |
| Example 32 | γ-globulin | 30 | 3.5 | 1.2 | 65.3 |

The results are shown in Table 12. No cracks were generated in all the coating layers prepared from the coating compositions of Examples 25 to 32.

TABLE 12

|  | Content ratio of L-arginine to physiologically active substance | Content [%] of glycerin | Cracks |
|---|---|---|---|
| Example 25 | 0.12 | 16.3 | ○ |
| Example 26 | 0.12 | 21.8 | ○ |
| Example 27 | 0.12 | 22.6 | ○ |

TABLE 12-continued

|  | Content ratio of L-arginine to physiologically active substance | Content [%] of glycerin | Cracks |
|---|---|---|---|
| Example 28 | 0.12 | 18.6 | ○ |
| Example 29 | 0.12 | 16.6 | ○ |
| Example 30 | 0.12 | 26.8 | ○ |
| Example 31 | 0.12 | 26.6 | ○ |
| Example 32 | 0.12 | 17.9 | ○ |

REFERENCE SIGNS LIST

1 . . . Microneedle device, 2 . . . Substrate, 3 . . . Microneedle, 5 . . . Coating layer, 10 . . . Coating composition, 11 . . . Mask plate, 12 . . . Spatula, 13 . . . Opening.

The invention claimed is:

1. A microneedle device, comprising:
 a substrate;
 a microneedle disposed on the substrate; and
 a coating layer formed on the microneedle;
 wherein the coating layer consists essentially of a physiologically active substance, arginine, and glycerin, a mass of the arginine being 0.06 to 0.85-fold of a mass of the physiologically active substance of the coating layer and a mass of the glycerin is 40% or less relative to a mass of the whole coating layer.

2. The microneedle device according to claim 1, wherein the coating layer further includes an acid selected from the group consisting of citric acid, phosphoric acid, boric acid, tartaric acid, and lactic acid.

* * * * *